(12) United States Patent
Hoock et al.

(10) Patent No.: US 8,962,847 B2
(45) Date of Patent: Feb. 24, 2015

(54) MULTICOMPONENT CRYSTALS MADE OF ([2-AMINO-6-(4-FLUORO-BENZYLAMINO)-PYRIDIN-3-YL]-CARBAMIC ACID ETHYL ESTER AND AN ARYLPROPIONIC ACID

(75) Inventors: Christoph Martin Hoock, Dresden (DE); Asal Qadan, Dresden (DE); Bernd Terhaag, Dresden (DE)

(73) Assignee: TEVA GmbH, Ulm (DE)

(*) Notice: Subject to any disclaimer, the term of this patent is extended or adjusted under 35 U.S.C. 154(b) by 0 days.

(21) Appl. No.: 13/992,248

(22) PCT Filed: Dec. 20, 2011

(86) PCT No.: PCT/EP2011/073442
§ 371 (c)(1),
(2), (4) Date: Jun. 7, 2013

(87) PCT Pub. No.: WO2012/084976
PCT Pub. Date: Jun. 28, 2012

(65) Prior Publication Data
US 2013/0267567 A1    Oct. 10, 2013

(30) Foreign Application Priority Data
Dec. 20, 2010   (DE) .................. 10 2010 063 609

(51) Int. Cl.
*A61K 31/44* (2006.01)
*C07D 213/75* (2006.01)
*A61K 31/192* (2006.01)

(52) U.S. Cl.
CPC ............. *A61K 31/44* (2013.01); *C07D 213/75* (2013.01); *A61K 31/192* (2013.01)
USPC ............................. 546/308; 514/353; 514/352

(58) Field of Classification Search
USPC ......................................... 514/352; 546/308
See application file for complete search history.

(56) References Cited

U.S. PATENT DOCUMENTS

| 4,690,823 A | 9/1987 | Lohner et al. |
| 4,778,799 A * | 10/1988 | Tibes et al. .................. 514/277 |

(Continued)

FOREIGN PATENT DOCUMENTS

| DE | 197 05 555 A1 | 8/1998 |
| EP | 0 158 913 A2 | 10/1985 |

(Continued)

OTHER PUBLICATIONS

Kornhuber L. et al.: Flupirtine shows functional NMDA receptor antagonism by enhancing Mg2+ block via activation of voltage independent potassium channels; Journal of Neural Transmission (1999) 106; 857-867.

(Continued)

*Primary Examiner* — John Mabry
*Assistant Examiner* — Daniel Carcanague
(74) *Attorney, Agent, or Firm* — Gudrun E. Huckett

(57) ABSTRACT

The invention relates to novel multicomponent crystals, to the production thereof, and to the use thereof for treating pain conditions, in particular of unclear genesis, by means of a simultaneous effect on pains which are caused by muscle tension or degenerative joint diseases as well as on pains that are caused by inflammatory processes. The multicomponent crystals according to the invention contain ([2-amino-6-(4-fluoro-benzylamino)-pyridin-3-yl]-carbamic acid ethyl ester (flupirtine) and an arylpropionic acid as the sole active ingredient combination and can be produced by dissolving flupirtine and the arylpropionic acid in an inert organic solvent and subsequently crystallizing the multicomponent crystal.

20 Claims, 13 Drawing Sheets

(56) References Cited

U.S. PATENT DOCUMENTS

Figure 1:
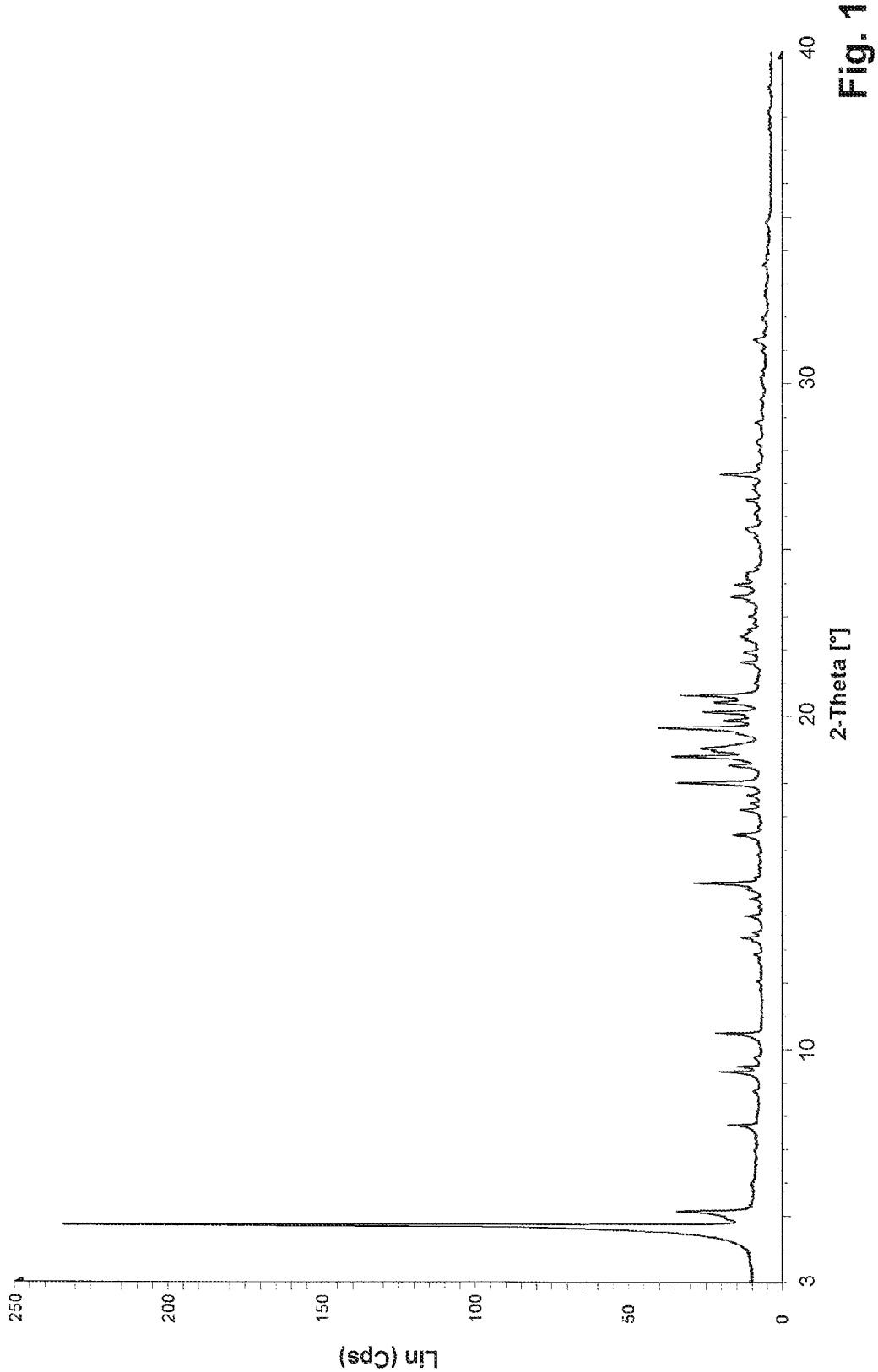

| | | |
|---|---|---|
| 5,959,115 A | 9/1999 | Olbrich et al. |
| 6,251,426 B1 | 6/2001 | Gullapalli |
| 2012/0028930 A1* | 2/2012 | Kalofonos et al. ............ 514/159 |
| 2013/0261157 A1* | 10/2013 | Hoock et al. .................. 514/353 |

FOREIGN PATENT DOCUMENTS

| | | |
|---|---|---|
| EP | 0 207 193 A2 | 1/1987 |
| EP | 1 697 005 B1 | 9/2006 |
| EP | 2 123 626 A1 | 11/2009 |
| WO | 2005/058319 A1 | 6/2005 |
| WO | 2006/024018 A2 | 3/2006 |
| WO | 2007/128056 A1 | 11/2007 |
| WO | 2009/152168 A2 | 12/2009 |
| WO | WO2010017343 * | 2/2010 |
| WO | WO2010043412 * | 4/2010 |

OTHER PUBLICATIONS

Kornhuber L. et al.: Neuronal Kaliumkanalöffnung durch Flupirtin; Fortschr. Neurol. Psychiat. 67 (1999) 466-475; Georg Thieme Verlag Stuttgart—New York; see English Abstract.

Lötsch J. et al.: Simultaneous fitting of R- and S-ibuprofen plasma concentrations after oral administration of the racemate; Clin. Pharmacol. 52, 387-398; May 25, 2001.

Rahlfs V.: Reevaluation of some double-blind, randomized studies of dexibuprofen (seractil): a state-of-the-art overview; J. Clin. Pharmacol. 1996; 36; 33S-40S.

Singer F. et al.: Evaluation of the efficacy and dose-response relationship of dexibuprofen (S(+)-ibuprofen) in patients with osteoarthritis of the hip and comparison with racemic ibuprofen using the WOMAC osteoarthritis index; International Journal of Clinical Pharmacology and Therapeutics; vol. 38—No. 1/2000 (15-24).

White P.F.: Can the use of specific isomers improve the safety and efficacy of nonsteroidal antiinflammatory drugs? Anesth. Analg. 2003:97:209-310.

Diamantis W: et al.: Alalgesic activity following combined oral administration of flupirtine maleate and peripherally acting analgesics in mice and rats; Postgraduate Medical Journal (1987) 63; 29-34; cited in international search report.

Zieglgänsberger W.: Neuronale Kaliumkanal-Öffnung und das besondere Wirkspektrum von Flupirtin; Schemrz 14 Suppl. 1 (1999) p. 13; translation attached.

* cited by examiner

MULTICOMPONENT CRYSTALS MADE OF ([2-AMINO-6-(4-FLUORO-BENZYLAMINO)-PYRIDIN-3-YL]-CARBAMIC ACID ETHYL ESTER AND AN ARYLPROPIONIC ACID

The present invention concerns novel multicomponent crystals of ([2-amino-6-(4-fluoro-benzylamino)-pyridin-3-yl]carbamic acid ethyl ester and an arylpropionic acid, their preparation as well as their use in pharmaceutical preparations. The pharmaceutical preparations according to the invention are suitable for treatment of pain conditions, in particular of unclear genesis, by a simultaneous action on pains caused by muscle tension or degenerative joint diseases as well as on those that are caused by inflammatory processes.

([2-amino-6-(4-fluoro-benzylamino)-pyridin-3-yl]carbamic acid ethyl ester, also known as flupirtine, is a centrally acting non-opioid analgesic substance that is free of the typical side effects of natural or synthetic opioids such as, for example, respiratory depression, constipation, development of drug tolerance, physical or psychological dependence or risk of addiction. Flupirtine is an active ingredient that can normalize an increased muscular tone.

Flupirtine is the prototype of a new class of analgesic substances with new specific and therapeutically relevant properties. In this context, the action mechanism of flupirtine is not based on a direct but on an indirect functional NMDA antagonistic effect. This mechanism results in three different action principles: analgesic, muscular tone-reducing, and neuroprotective. The various actions of flupirtine are the result of a single molecular action mechanism, i.e., the action of flupirtine as a selective neuronal potassium channel opener (selective neuronal potassium channel opener=SNEPCO) (Kornhuber J et al. (1999); Kornhuber J et al, (1999a)); Ziegl-gänsberger W. Neuronale Kaliumkanal-Öffnung und das besondere Wirkspektrum von Flupirtin. Schmerz 14 Suppl. 1 (1999) p. 13) that represents a new principle in pain therapy.

As a result of these multiple actions, flupirtine exhibits a unique and broad pharmacological action spectrum. Flupirtine is suitable for treatment and prophylaxis of acute and chronic pain, including neuropathic pain, nerve pain, pain caused by cancer diseases, vasomotoric and migraine headaches, pain conditions after operations, after injuries, burns, in case of dysmenorrhea, toothache and arthritic pain. Anti-inflammatory effects of flupirtine are to be expected for conventional analgesic dosages only to a minimal degree because a satisfactory anti-inflammatory action has been observed in animal experiments only upon very high dosages (>30 mg per kg body weight). Flupirtine is primarily effective in the treatment and prophylaxis of pains that in particular are caused by muscle tension, muscle spasms and muscle stiffness. It is particularly effective for the treatment of back pain wherein a clear differential diagnosis regarding the genesis of this tension-caused back pain in the meaning of inflammatory and/or non-inflammatory causes cannot always be determined unequivocally for an individual case.

Flupirtine maleate can be combined with various pain relievers, for example, with morphine (EP 0977736), with NK (neurokinin) antagonists (WO 2007/1128056), with tramadol (EP 1697005) or also paracetamol (EP 207193).

(RS)-2-[4-(2-methylpropyl)-phenyl]propanoic acid (ibuprofen) and its enantiomer dexibuprofen, also known as (+)-(2S)-2-[4-(2-methylpropyl)-phenyl]propanoic acid or (S)-ibuprofen, belongs to the group of non-steroidal antirheumatic agents/antiphlogistic agents (NSAIDS). They inhibit non-selectively the cyclooxygenases (COX) I and II which are responsible for the generation of inflammation-mediating prostaglandins in the organism.

Ibuprofen is a pharmaceutical substance that is used for the treatment of pains, inflammations, and fever. Chemically, it belongs to the group of arylpropionic acids. It has pain-relieving (analgesic), inflammation-inhibiting (antiphlogistic) and fever-suppressing (antipyretic) action.

Dexibuprofen was described in EP 158913 and is an effective non-steroidal anti-inflammatory pharmaceutical substance for patients with painful hip osteoarthritis. In comparison with racemic ibuprofen, half of the daily dosage of dexibuprofen exhibits an at least identical efficacy (F. Singer, et al., Int. J. Clin. Pharm. Ther., 38(1), 25-29 (2000); V. W. Rahlfs, J. Clin. Pharmacol 36, pp. 33-40, (1996)). Therefore, a reduced substance quantity per dosage unit is sufficient. Also, the action begins somewhat faster than with the racemic mixture of ibuprofen (L. Lötsch, et al, Br. J. Clin Pharmacol 52, 387-398, 2001). While a reduction of pain and fever in general occurs within 1 hour after taking the first dosage, it takes generally several days to weeks until the inflammation-inhibiting action of these agents begin (Physician's Desk Reference, 53rd ed., 1667-76 (1999)).

Soft gelatin capsules containing ibuprofen are known from U.S. Pat. No. 4,690,823 and also U.S. U.S. Pat. No. 6,251,426.

Among the NSAIDS, arylpropionic acids such as ketoprofen, naproxen, ibuprofen and in particular dexibuprofen are considered as being especially low in side effects (P. F. White (2003). Anesth Analg. 97(2): pp. 309-310).

The simultaneous administration of flupirtine maleate and various NSAIDS is discussed in a scientific publication (Diamantis, W; Gordon, R. Postgrad Med J 1987, 63 Suppl 3 (29-34). Already at a very low dosage (15 mg per kg, mice; 35 mg per kg; rat), flupirtine maleate enhances in combination with various dosages of NSAIDS analgesic substances the antinociceptive (i.e., pain perception inhibiting) activity of paracetamol, acetyl salicylic acid, and diclofenac.

The synergistic combination of flupirtine salts with various non-steroidal antiphlogistic agents is disclosed in DE 36 65 538.4. Here it was found that the action of flupirtine maleate is surprisingly enhanced by combination with certain non-steroidal antiphlogistic substances synergistically wherein at the same time the action of the antiphlogistic substances also is experiencing a synergistic increase. In this connection, flupirtine is used as maleate, gluconate, or hydrochloride. Especially preferred is the combination with diclofenac potassium salt.

The patent application WO 2005/058319 A1 discloses the use of flupirtine maleate for the treatment of neuropathic pain or pain in conjunction with an inflammation wherein optionally a further analgesic compound, for example, a non-steroidal antirheumatic agent, is additionally administered.

Many of the disclosed NSAIDS cause however a broad spectrum of side effects. For diclofenac, for example, the following typical side effects are described: gastric and intestinal problems that are caused by an inhibition of cyclooxygenase I that exists in the gastric mucosa. Moreover, disruptions in hematopoiesis and hypersensitivity reactions may occur, for example, hypersensitivity of the skin relative to sunlight. In addition, an increase in liver function readings may happen (for example, transaminases). Since dizziness and fatigue may occur, the operation of machinery and participation in traffic requires caution (physician's information on didofenac). The active ingredients isoxicam and sulindac that are also disclosed are not approved in Germany, inter alia as a result of their side effects. Acetyl salicylic acid also has a great side effect potential on the stomach and can also trigger the Reye syndrome. Paracetamol is in itself already a problem for the liver and should therefore not be combined with flupirtine under any circumstance.

The above mentioned side effects have the result that, in addition to the beneficial antinociceptive and anti-inflammatory effects, also the side effects of flupirtine, such as fatigue or a possible increase of transaminases, may increase in case of a physical combination of flupirtine with NSAIDs. Moreover, for a purely physical mixture of the individual components, as disclosed in DE 36 65 538.4, it is very difficult to achieve a uniform absorption in the gastrointestinal tract due to the different solubility and different dissolving speed. Moreover, separation may occur because of the different crystal forms and different densities of the active ingredients. A stable formulation of the components with satisfactory bioavailability is therefore not to be expected for these mixtures.

By formation of a multicomponent crystal of an active ingredient with another suitable active ingredient, a new solid material is formed whose physical properties differ significantly from those of the individual components. Affected parameters are inter alia in this context solubility, dissolving speed, melting point as well as particle shape and size.

EP 2 123 626 A1 claims co-crystals of duloxetine with at least one co-crystal former that is suitable for pain treatment. Duloxetine is an active ingredient of the group of selective serotonin-norepinephrine reuptake inhibitors and is used inter alia for the treatment of depressions and anxiety disorders. A co-crystal of duloxetine and S-naproxen is mentioned as a co-crystal.

Such multi-component crystals differ from the purely physical mixture of the two partners also with regard to crystallographic and spectroscopic properties. Suitable measuring methods for the detection of solid state properties of these new compounds are inter alia X-ray crystallography of the powder (XRPD) or of the single crystal; solid-state NMR (ssNMR), Raman spectroscopy or also differential scanning calorimetry (DSC).

The object of the present invention is to provide a new substance which exhibits the unique analgesic action of the selective potassium channel opener (SNEPCO) flupirtine as well as the pharmacologically known action spectrum, such as inflammation-inhibiting and analgesic activity, of an arylpropionic add such as ibuprofen or dexibuprofen, that is poor in side effects and can be easily formulated as a pharmaceutical solid administration form without exhibiting the typical problems of physical mixtures such as different bioavailability or separation during the production process.

Moreover, the new substance should be acting effectively against pains caused inter alia by tension as well as against those that are caused by inflammatory processes so that a treating physician can administer the medicament even for pains of unclear genesis and does not expose the patient thereby to additional unacceptable side effects.

The object is solved according to the invention by novel multi-component crystals of flupirtine ((([2-amino-6-(4-fluoro-benzylamino)-pyridin-3-yl]carbamic acid ethyl ester) and an arylpropionic acid, selected from ibuprofen and dexibuprofen, in particular by a multicomponent crystal that contains as the sole active ingredient combination the components ([2-amino-6-(4-fluoro-benzylamino)-pyridin-3-yl] carbamic acid ethyl ester (flupirtine)) and an arylpropionic acid, selected from ibuprofen and dexibuprofen.

Multicomponent crystal in the meaning of the invention is to be understood as a crystal that is comprised either of neutral or of ionic components wherein neutral components are used for crystallization but during crystallization to the multicomponent crystal also ionic components may be generated. A multicomponent crystal thus either is a co-crystal, a salt, a solvate or a mixed form that comprises co-crystal as well as salt proportions.

A co-crystal in the meaning of the invention is a crystalline structure which is comprised of two or more neutral compounds.

In contrast to a purely physical mixture of the starting materials, a multicomponent crystal according to the invention is characterized advantageously by changed physicochemical properties which, for example, affect the solubility, stability, hygroscopicity, handling, and tablet-forming property, and that enable its unequivocal characterization.

Surprisingly, the inventors have found that from flupirtine and arylpropionic acids, such as ibuprofen and dexibuprofen, by heating, dissolving or grinding them jointly, novel multicomponent crystals, in particular co-crystals of ([2-amino-6-(4-fluoro-benzylamino)-pyridin-3-yl]carbamic acid ethyl ester (flupirtine) and an arylpropionic acid, selected from ibuprofen and dexibuprofen, can be obtained. This is surprising because up to now only the unbranched alkane (or alkene) carboxylic acids from the group of carboxylic acids yielded flupirtine salts.

The multicomponent crystal of flupirtine and ibuprofen in accordance with the invention is preferably characterized by an X-ray powder diffractogram measured by using Cu $K_{\alpha 1}$ radiation and a Johansson germanium single crystal monochromator with a step width of 0.00922° in the diffraction angle range of 2θ=3–80° C. with a characteristic peak at 2θ=4.7±0.2°. Preferably, the multicomponent crystal of flupirtine and ibuprofen is additionally characterized by further characteristic peaks at 2θ=5.1±0.2°, 7.7±0.2° 9.3±0.2° and 10.4±0.2°. Particularly preferred, it has further characteristic peaks at 2θ=18.0±0.2°, 20.6±0.2°, and 27.3±0.2°.

In a preferred embodiment, the multicomponent crystal according to the invention of flupirtine and ibuprofen is characterized by an X-ray powder diffractogram substantially as shown in FIG. 1.

Figure 3:
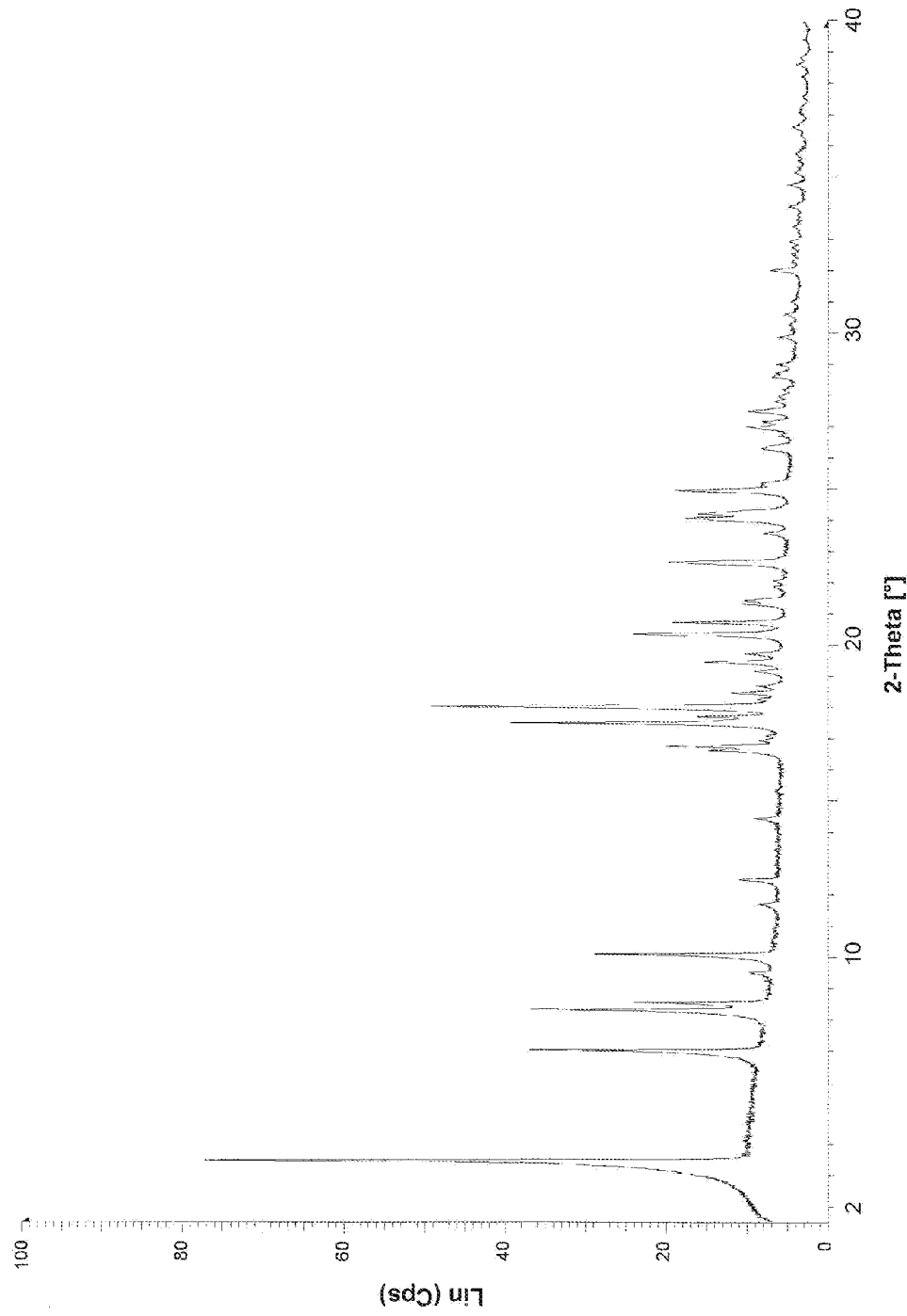

The multicomponent crystal of flupirtine and ibuprofen according to the invention is moreover preferably characterized by a DSC (differential scanning calorimetry) thermogram as shown in FIG. 3. It has a characteristic melting endothermal peak in the range of 56 to 70° C. with an onset temperature at 56.9±2° C. and a signal maximum at 64.7±3° C.

Figure 2:
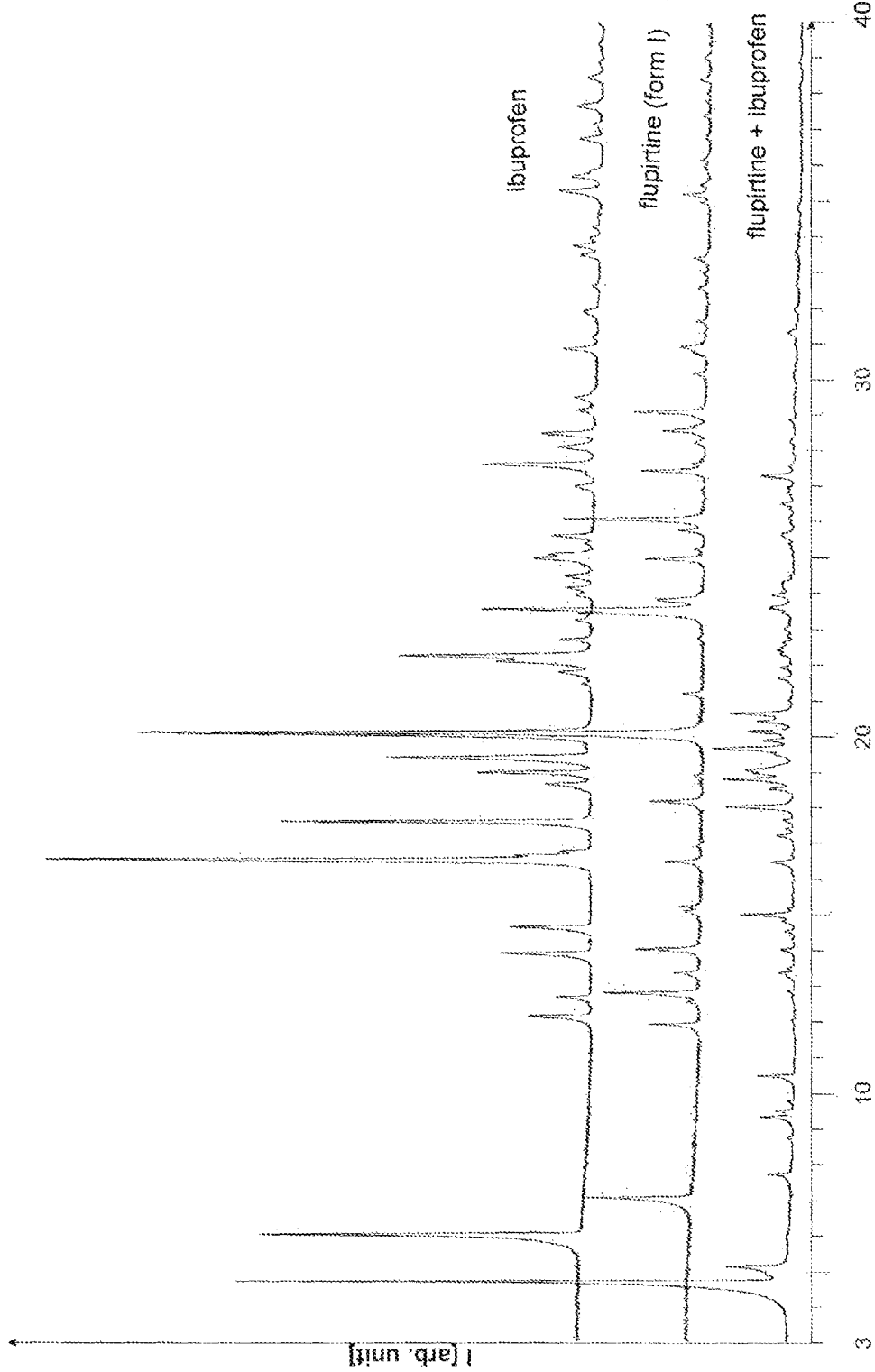

The multicomponent crystal according to the invention of flupirtine and dexibuprofen is preferably characterized by an X-ray powder diffractogram measured by using Cu $K_{\alpha 1}$ radiation and a Johansson germanium single crystal monochromator with a step width of 0.00922° in the diffraction angle range of 2θ=3–80° C. with a characteristic peak at 2θ=3.4±0.2°. Preferably, the multicomponent crystal of flupirtine and dexibuprofen is additionally characterized by further characteristic peaks at 2θ=8.3±0.2°, 10.1±0.2° 16.7±0.2°, 17.5±0.2°, and 20.7±0.2°. Preferably, in addition it is characterized by further characteristic peaks at 2θ=12.5±0.2°, 14.4±0.2°, and 24.2±0.2°. In a further embodiment, the multicomponent crystal of flupirtine and dexibuprofen according to the invention is characterized by X-ray powder diffractogram substantially as shown in FIG. 2.

Figure 4:
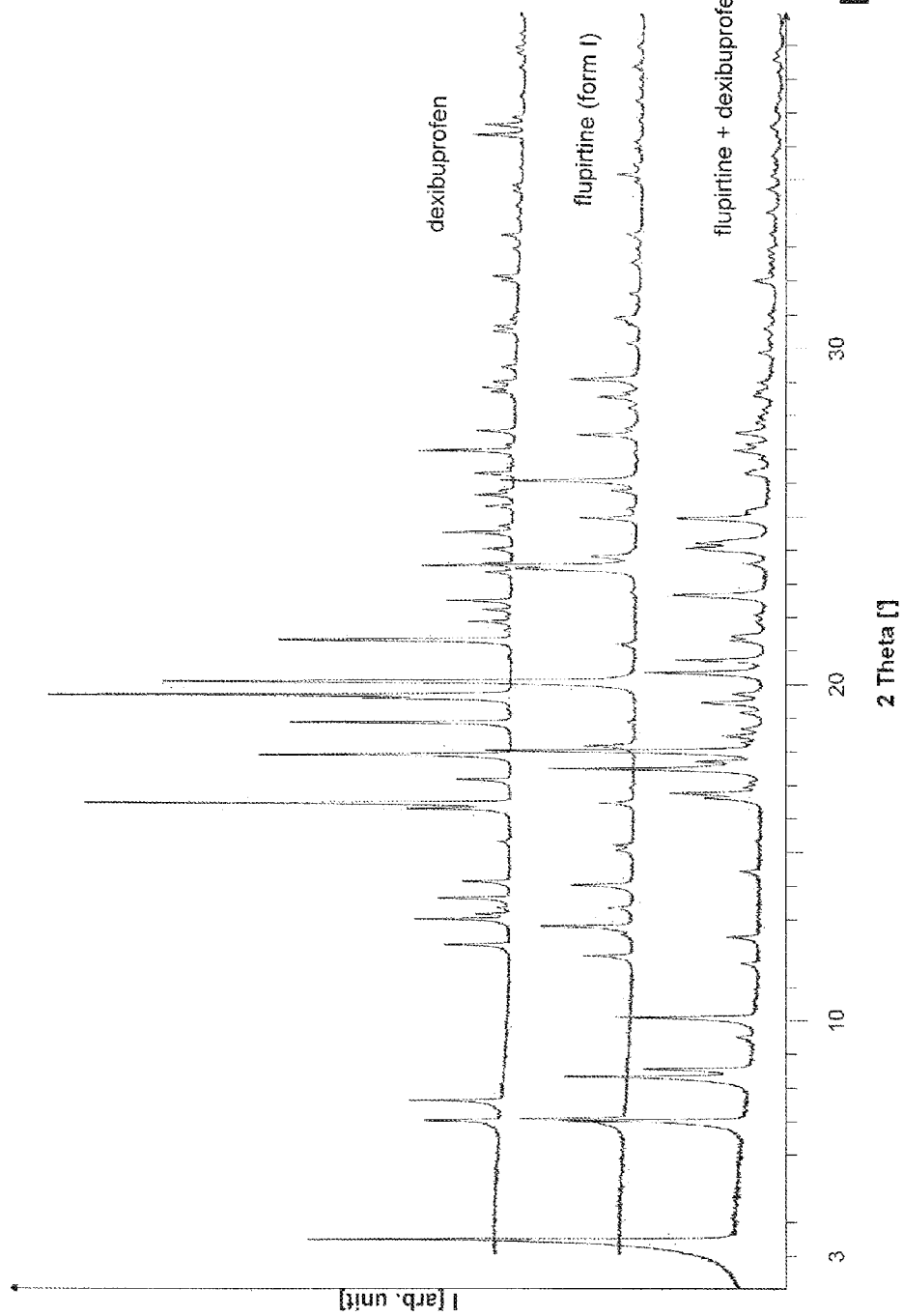

The multicomponent crystal of flupirtine and dexibuprofen according to the invention is preferably characterized by DSC (differential scanning calorimetry) thermogram as shown in FIG. 4. It has a characteristic melting endothermal peak in the range of 73 to 85° C. with an onset temperature at 75.9° C. and a signal maximum at 81.4° C.

Preferably, the multicomponent crystals according to the invention of flupirtine and an arylpropionic acid, selected from ibuprofen and dexibuprofen, are comprised of equimolar quantities of the two components wherein also minimal deviations of 10%, preferably 5%, especially preferred 2%, of the molar ratio are still encompassed by the invention inasmuch as macroscopically a uniform compound results. The molar ratio of the compounds is thus preferably in the range of 1:0.9 to 1:1.1, preferably of 1:0.95 to 1:1.05, more preferred 1:0.98 to 1:1.02. Especially preferred, the molar ratio of the components is 1:1.

The multicomponent crystals according to the invention can be prepared inter alia in a melting reaction in which the starting materials flupirtine and ibuprofen or dexibuprofen are melted together and cooled, whereby products are partially obtained as amorphous glass-like melts that upon further treatment such as grinding with cooling, variable temperature gradients or ultrasound treatment can be transferred into granular, partially also crystalline, forms.

Moreover, the multicomponent crystals according to the invention are also obtainable by dissolving them together in a suitable solvent and subsequently allowing them to crystallize. Granular products are also obtained by grinding of an equimolar quantities of flupirtine with the arylpropionic acids or by preparation in solution.

Subject matter of the invention is therefore also a method for producing a multicomponent crystal according to the invention of flupirtine and ibuprofen, wherein flupirtine and ibuprofen are together dissolved in a suitable inert organic, preferably aprotic, solvent, preferably 2-propanol. Preferably, this is done with heating of the mixture, preferably to a temperature between 50 and 80° C., particularly preferred between 60 and 70° C. Subsequently, the multicomponent crystal according to the invention crystallizes from the solution. This is done preferably with cooling of the solution to room temperature and/or by concentrating the solution. The obtainable multicomponent crystal is subsequently purified and/or dried in a known manner.

Subject matter of the invention is moreover also a method for producing a multicomponent crystal according to the invention of flupirtine and dexibuprofen wherein flupirtine and dexibuprofen are together dissolved in a suitable inert organic, preferably aprotic, solvent, preferably acetone. Preferably, this is done with heating of the mixture, preferably to a temperature between 30 and 70° C., particularly preferred between 40 and 60° C. Subsequently, the multicomponent crystal according to the invention crystallizes from the solution. This is done preferably with cooling of the solution to room temperature and/or by concentrating the solution. The obtainable multicomponent crystal is subsequently purified and/or dried in a known manner.

The preparation according to the invention contains the multicomponent crystals of flupirtine and arylpropionic acid in accordance with the invention optionally in admixture with other pharmacologically or pharmaceutically active substances. The preparation of the medicament is done in a known way, wherein the known and conventional pharmaceutical excipients as well as other conventional carrier and diluting agents can be used.

Subject matter of the invention is moreover a pharmaceutical preparation which contains the multicomponent crystals according to the invention of flupirtine and arylpropionic acid selected from ibuprofen and dexibuprofen.

Methods for determining an effective administration quantity of the preparation according to the invention for therapeutic and prophylactic purposes are known to a person of skill in the art. In order to be able to employ the analgesic effect (inter alia by affecting muscle tension pain) as well as the anti-inflammatory effect of the preparation according to the invention, a daily dosage of 50 mg to 1.000 mg, preferably 200 mg to 800 mg, is administered.

By means of the new multicomponent crystals according to the invention of flupirtine and an arylpropionic add selected from ibuprofen and dexibuprofen, the pharmaceutically inactive components of the base compound (such as maleate, hydrochloride, mesilate etc.) as well as of the acid component (such as sodium, potassium, ammonium etc.) are avoided; advantageously, in case of solid oral administration forms, this leads to a reduction of the quantity to be administered and of the required volume of the administration form. The uniform shape of the multi-component crystal prevents advantageously also the separation of the components during processing and facilitates thus their exact dosage.

An administration unit can be administered, for example, 1 to 5 times, preferably t to 3 times, preferably 2 times daily.

The pharmaceutical preparation according to the invention can be administered in various ways known from pharmacology or medicine, for example, orally, parenterally, intraperitoneally, intravenously, sublingually, intramuscularly, rectally, transdermally, locally by a catheter or stent, subcutaneously, intraadiposaily, intraarticularly or intrathecally. Preferred is oral or rectal administration of the pharmaceutical preparation.

Suitable solid administration forms for oral administration include tablets, effervescent tablets, capsules, soft capsules, pills, powders, granulates, pellets and the like.

The release of the active ingredients from the pharmaceutical preparation according to the invention can be realized quickly or with retardation.

As a pharmaceutically acceptable carrier or filler various conventional excipients such as, for example, cellulose derivatives, starch derivatives, lactose, mannitol, dextrose, saccharose, calcium carbonate, magnesium oxide, magnesium stearate, talcum, starch, gelatine, gum Arabic, or the like or conventional inert solvents can be used.

Solid administration forms comprise optionally further conventional excipients such as glidants, binding agents, filling agents (such as for example, silicon dioxide, in particular porous amorphous silicon dioxide "Syloid", carbomer, guar gum, cellulose, microcrystalline cellulose, the cellulose ethers, cellulose esters, polyvinyl pyrrolidone as well as copovidone), release agents, lubricants, disintegrants (such as, for example, cross-linked polyvinyl pyrrolidone, sodium carboxylmethyl starch; sodium carboxyl methyl cellulose, corn starch, potato starch, croscarmellose sodium, crospovidone, guar gum, primogel), antioxidants, stabilizers, sweeteners, flavoring agents, dyes; solutizers (such as for example cyclodextrine and cyclodextrine derivatives) and/or emulsifiers (such as e.g. lecithin, pectin).

Further excipients are e.g. dry binding agents such as starch and starch derivatives, microcrystalline cellulose; highly dispersed silicon dioxide, mannite, lactose, moreover polyethylene glycol, in particular with a molecular weight of 4,000 to 6,000, crosslinked polyvinyl Pyrrolidone® (Polyplasdone®XL or Kollidon®L), crosslinked carboxyl methylcellulose (Acdisol®RCMC-XL), or dicalcium phosphate.

As excipients, moreover glidants, lubricants or mold release agents, for example, siliconized talcum, aluminum stearate, magnesium stearate, stearic acid, palmitic acid, stearyl, cetyl; and myristyl alcohol, paraffin, or hydrogenated fats are advantageous.

The solid administration forms can be coated with sucrose, with a cellulose derivative, polyacrylate derivative, phthalate derivative or other suitable substances, or they can be treated such that they have an extended or retarded action and such that they continuously release a predetermined quantity of an active ingredient. The invention comprises therefore also a pharmaceutical preparation that is characterized by a polymer film coating that acts as a retarding component and optionally contains release agents, binding agents, pigments or other pharmaceutical excipients. Preferably, the polymer film coating comprises at least one polymer selected from methacrylic acid; methacrylic ester (such as Eudragit®L and/or Eudragit®S), copolymers of acrylic and methacrylic acid esters; preferably with a low contents of trimethyl ammonium methacrylate (such as Eudragit®RL and/or Eudragit®RS), copolymers of acrylic acid and methacrylic acid as well as their esters (ratio of free carboxyl groups to ester groups e.g. 1:1) such as Eudragit®L30D, copolymers of ethyl acrylate and methylmethacrylate (such as Eudragit®NE 30 D), or mixtures thereof.

By dissolving or suspending, liquid formulations can be obtained also that are suitable for infusion or injection.

As non-aqueous solvents, for example, propylene glycol, polyethylene glycol and/or organic esters such as ethyl oleate can be used. Examples of oils are paraffin as well as animal, plant or synthetic oils such as e.g. peanut oil, castor oil, sesame oil, cotton seed oil, corn oil, wheat germ oil, soybean oil, mineral oil, olive oil, sunflower seed oil or liver oil, in particular cod liver oil.

By mixing with non-aqueous solvents or oils, viscous to semi-solid formulations can be obtained which can be filled particularly well into soft capsules. These capsules, despite their relatively high active ingredient contents of 50 to 600 mg, can be easily swallowed as a result of their elastic envelope and consistency of the contents.

For the multicomponent crystals according to the invention of flupirtine and an arylpropionic acid selected from ibuprofen and dexibuprofen, a mixture of glycol derivatives such as e.g. diethylene glycol monoethylether or polyethylene glycol, surface active agents such as e.g. glycerin derivatives, as well as thickening agents such as e.g. polyvinyl pyrrolidone has been found to be a suitable carrier substance for a soft capsule formulation. Neutral solutizers (dispersants and surface active agents) such as glycerides (also polyoxylglycerides), poly alkylene glycol ether, caprylocaproyl, or sugar esters stabilize and homogenize the mixtures with the active ingredients according to the invention.

Due to the minimal polarity of the new multicomponent crystal according to the invention, liquid and semi-solid formulations are suitable also for the transdermal administration, quite in contrast to a purely physical mixture of the components. Particularly suitable as a carrier for the multicomponent crystal according to the invention is a mixture comprising a carbomer, one or several fatty acid esters, a polyethylene glycol and one or several low-molecular weight alcohols.

All multicomponent crystals according to the invention of flupirtine and an arylpropionic acid selected from ibuprofen and dexibuprofen are characterized by low melting points (<70° C.); this is a particular challenge for solid oral administration forms in the form of tablets. Surprisingly, according to the method disclosed in DE 19705555 A1, by mixing the active ingredient with porous amorphous silicon dioxide a granular material can be obtained that can be pressed without problems to tablets with up to 600 mg of active ingredient. Preferably, in a tablet 0.5 to 8% of porous amorphous silicon dioxide are contained, based on the total weight.

The synergistic action of the two components flupirtine and arylpropionic acid can be demonstrated by animal model with the methods disclosed in DE 36 65 538. The methods disclosed therein are herewith incorporated as a reference. Also, it was possible to demonstrate that by administering a dosage of the component crystals according to the invention of flupirtine-dexibuprofen a significantly stronger effect on the pain occurs (writhing test with 0.8% acetic add). Moreover, in an inflammation model on the rat (carrageenan edema) a weak inflammation inhibition was observed with the examined dosage.

Multicomponent crystals of ([2-amino-6-(4-fluoro-benzylamino)-pyridin-3-yl]carbamic acid ethyl ester and an arylpropionic acid are particularly advantageous when the arylpropionic acid is (+)-(2S)-2-[4-(2-methylpropyl)-phenyl] propanoic acid (dexibuprofen). In this context, in comparison to the combination of ([2-amino-6-(4-fluoro-benzylamino)-pyridin-3-yl]carbamic acid ethyl ester and the enantiomeric mixture (RS)-2-[4-(2-methylpropyl)-phenyl]propanoic acid (ibuprofen), a faster action onset was determined and the same action effect can be achieved with a smaller dosage. In this way, advantageously the quantity of active ingredient to be administered and thus also the mass of the pharmaceutical formulation with same action strength can be reduced.

An aspect of the invention is also the use of the multicomponent crystals according to the invention of flupirtine and an arylpropionic acid selected from ibuprofen and dexibuprofen for treatment and prophylaxis of acute and chronic pains, including neuropathic pain, back pain, nerve pain, pain caused by fibromyalgia, pain caused by cancer diseases, vasomotoric and/or migraine or tension-caused headaches, pain conditions after operations, after injuries, burns, chemical burns, in case of dysmenorrhea, prophylaxis of muscle tension, toothache and arthritic pain as well as for the treatment of inflammation pain or pain of unclear genesis inasmuch as an inflammatory component of the pain is excluded.

The preferred administration duration is 1-2 days up to 6 weeks.

By the advantageous combined effect of the multicomponent crystals according to the invention of flupirtine and an arylpropionic acid selected from ibuprofen and dexibuprofen against non-inflammation-caused pain (as e.g. muscle tension-caused pain) and inflammation pain, the new active ingredient is particularly well suited for treatment of pain of unclear genesis of the musculoskeletal system, including the back, because here, as is known, inflammatory processes and muscle tension occur particularly frequently.

Subject matter of the invention is therefore also the use of a multicomponent crystal according to the invention for simultaneous treatment of pain of different causes, in particular of inflammatory pain, particular preferred of inflammatory-rheumatic pain of the spine and of soft tissue and of pain caused by muscle tension.

For example, tablets of different size can be produced, for example with a total weight of approximately 50-800 mg. They contain the multicomponent crystal according to the invention in the aforementioned quantities as well as conventional carrier substances and/or diluting agents and/or excipients. These templates can also be used for administering partial doses. In an appropriate way, also other preparations, for example, gelatin capsules or retard forms can be formulated.

For a faster dissolving action and improved bioavailability, the multicomponent crystals can also be administered as soft capsules. Here, the active ingredients are homogenously distributed in a soft gel matrix, i.e., suspended, dissolved or partially dissolved. Despite additional ingredients, these capsules as a result of their soft shelf can be easily swallowed.

Figure 5:
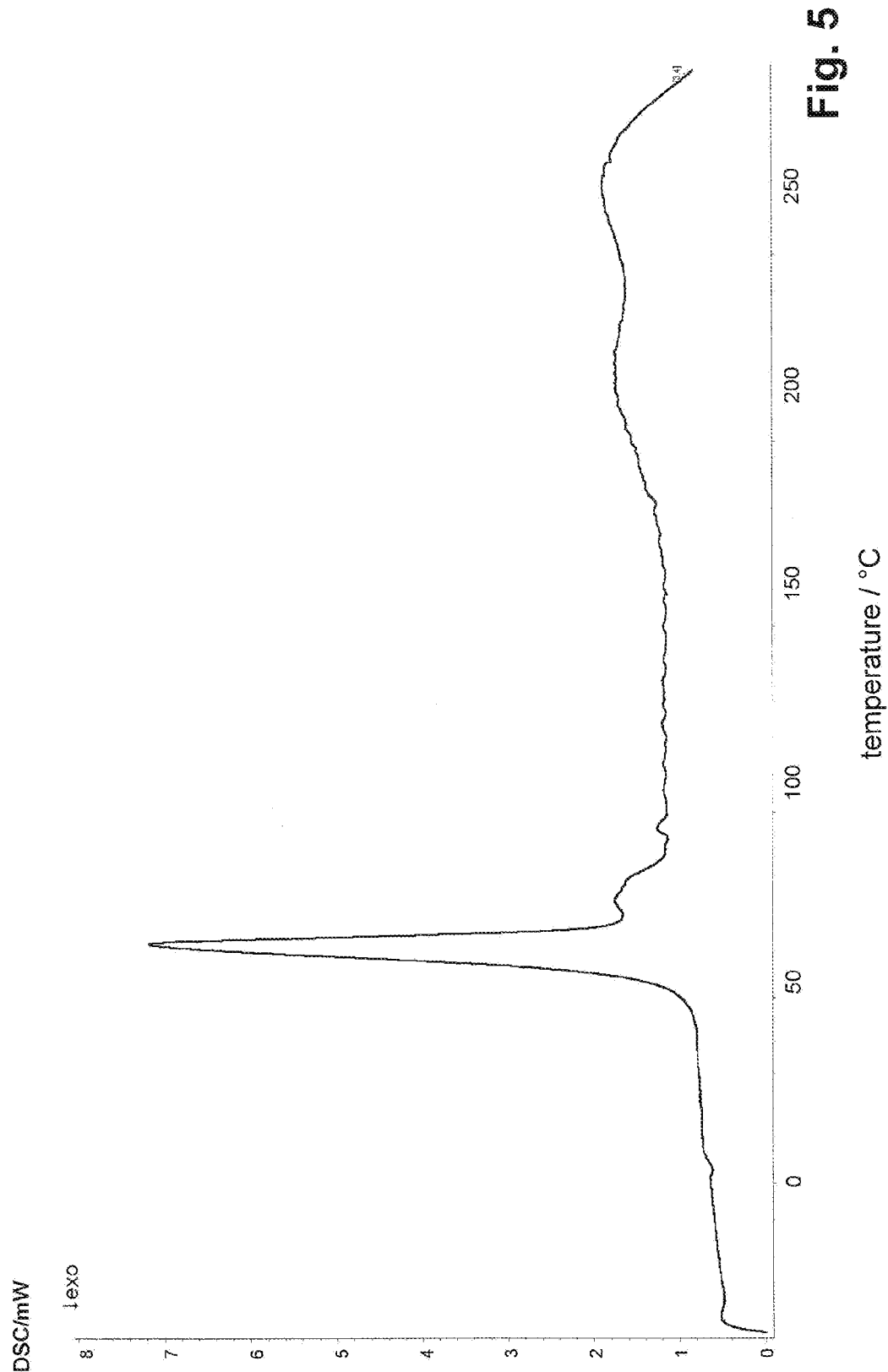
Figure 6:
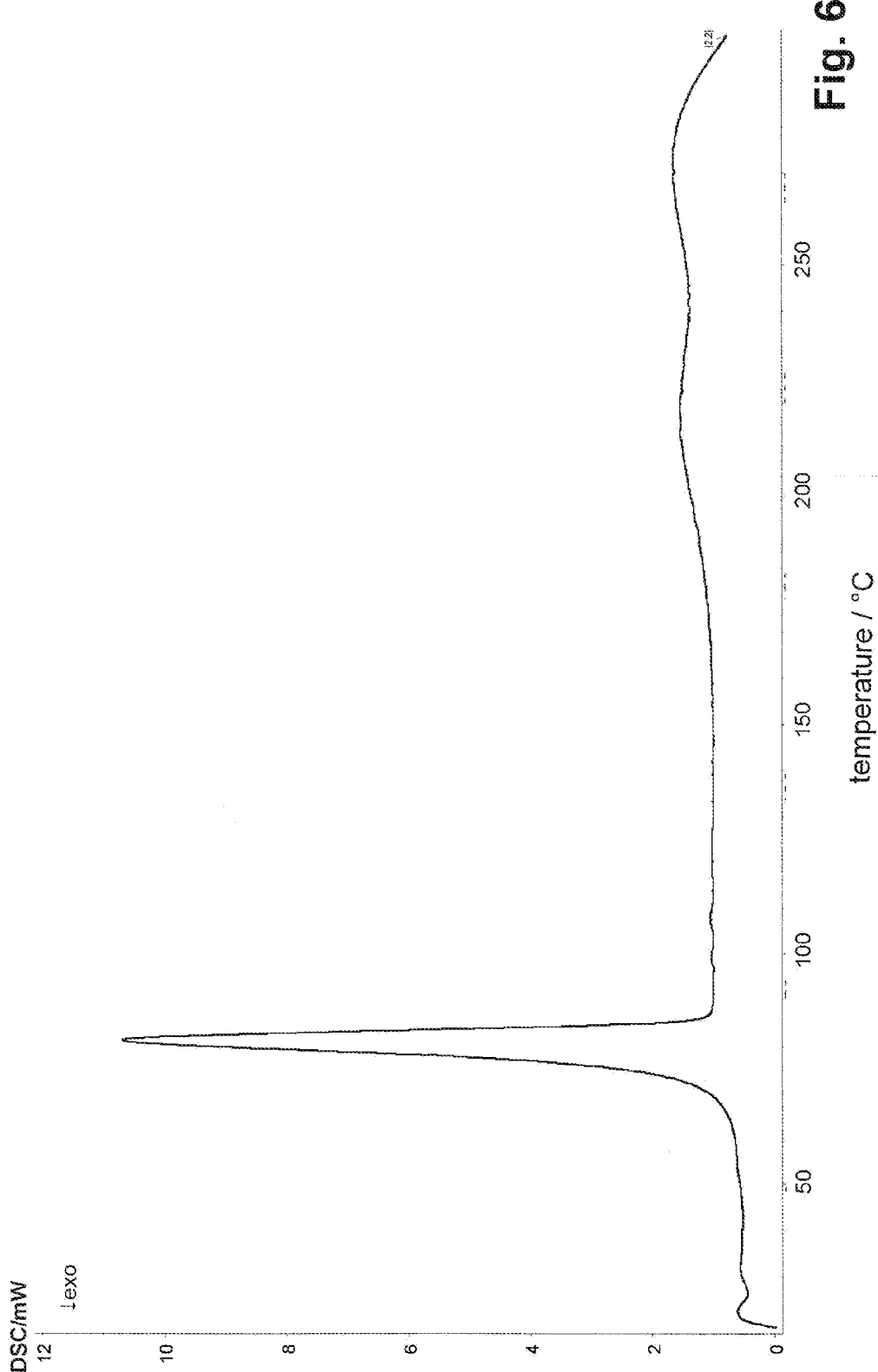
Figure 7:
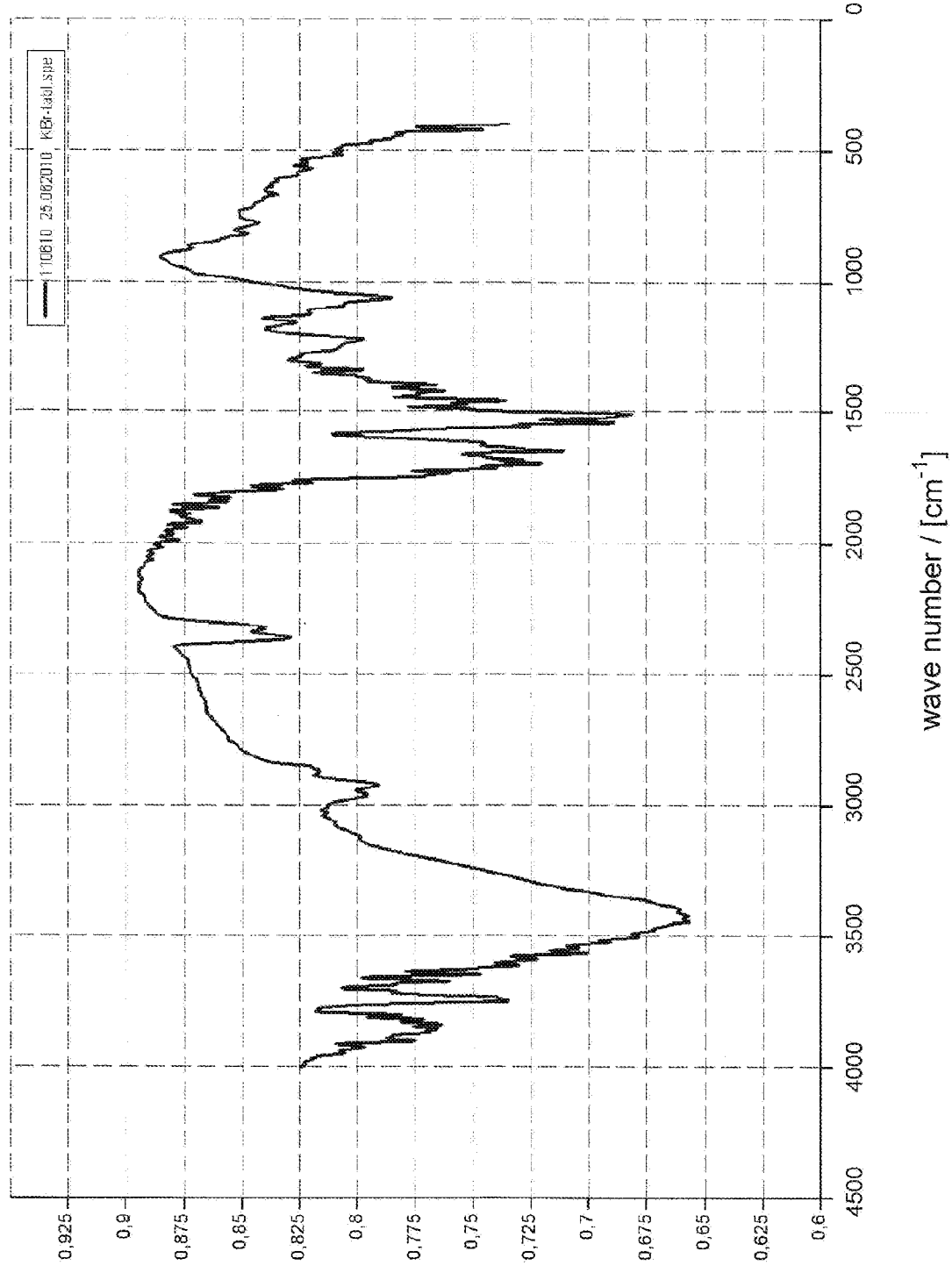
Figure 8:
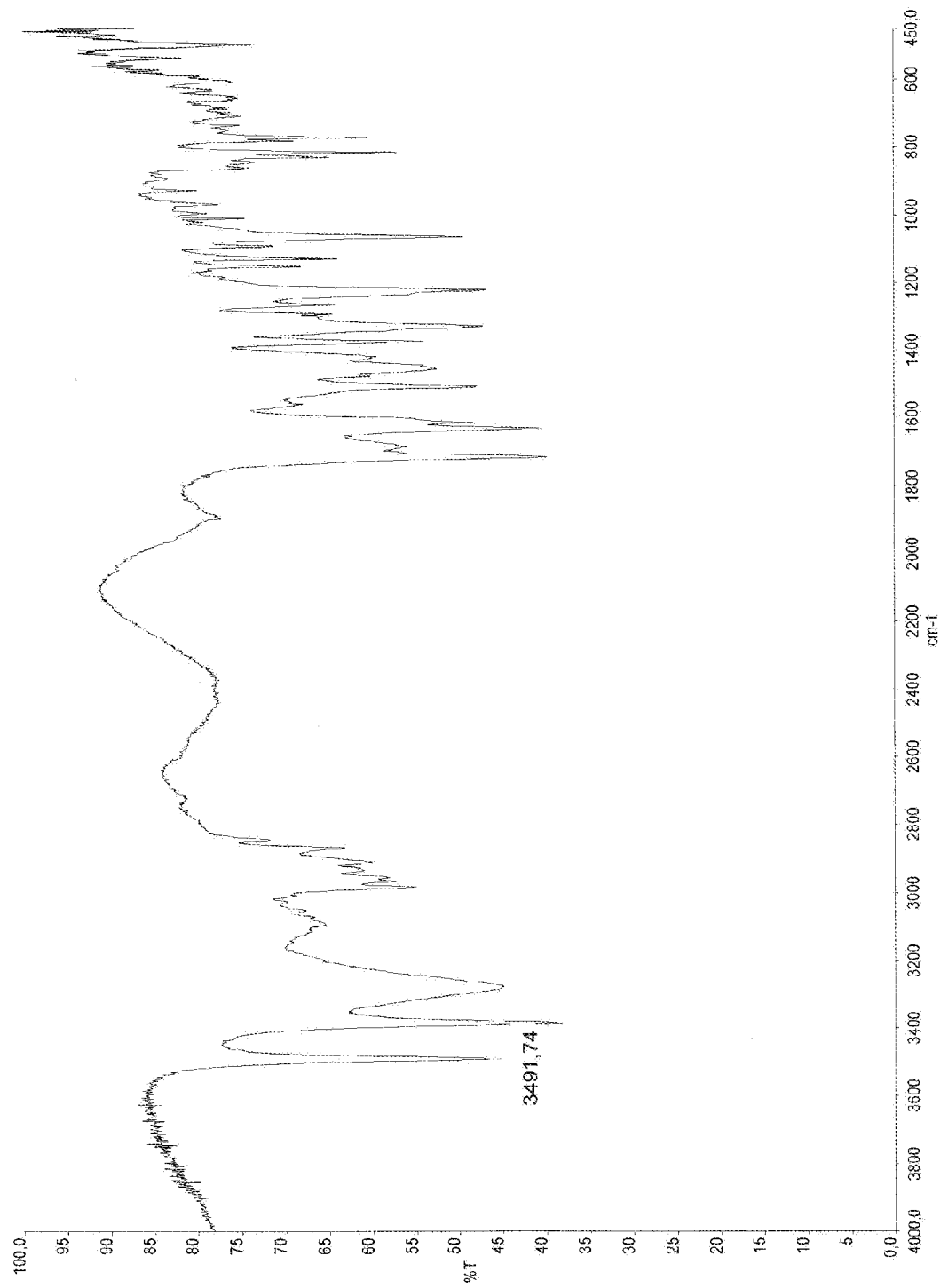
Figure 9:
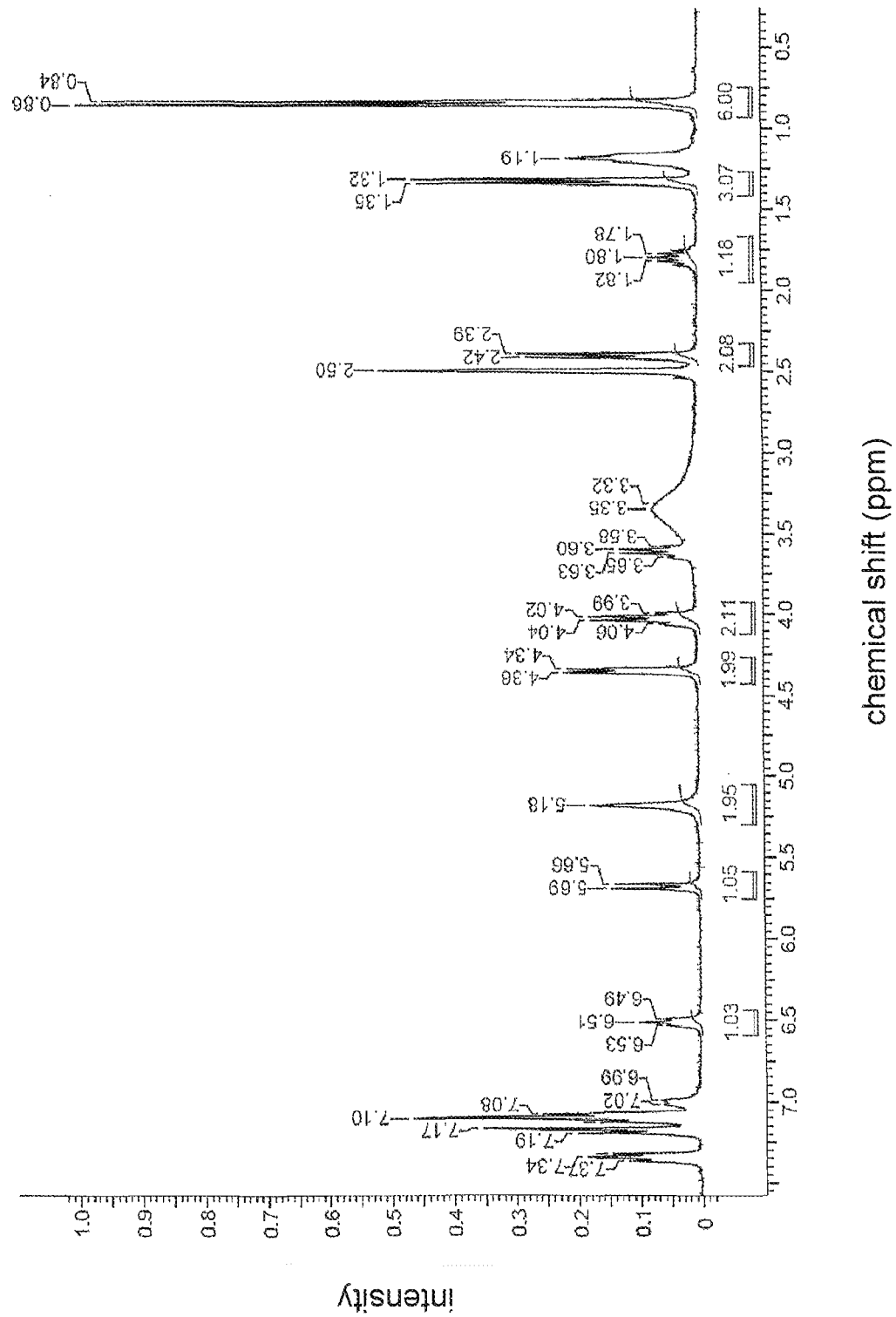
Figure 10:
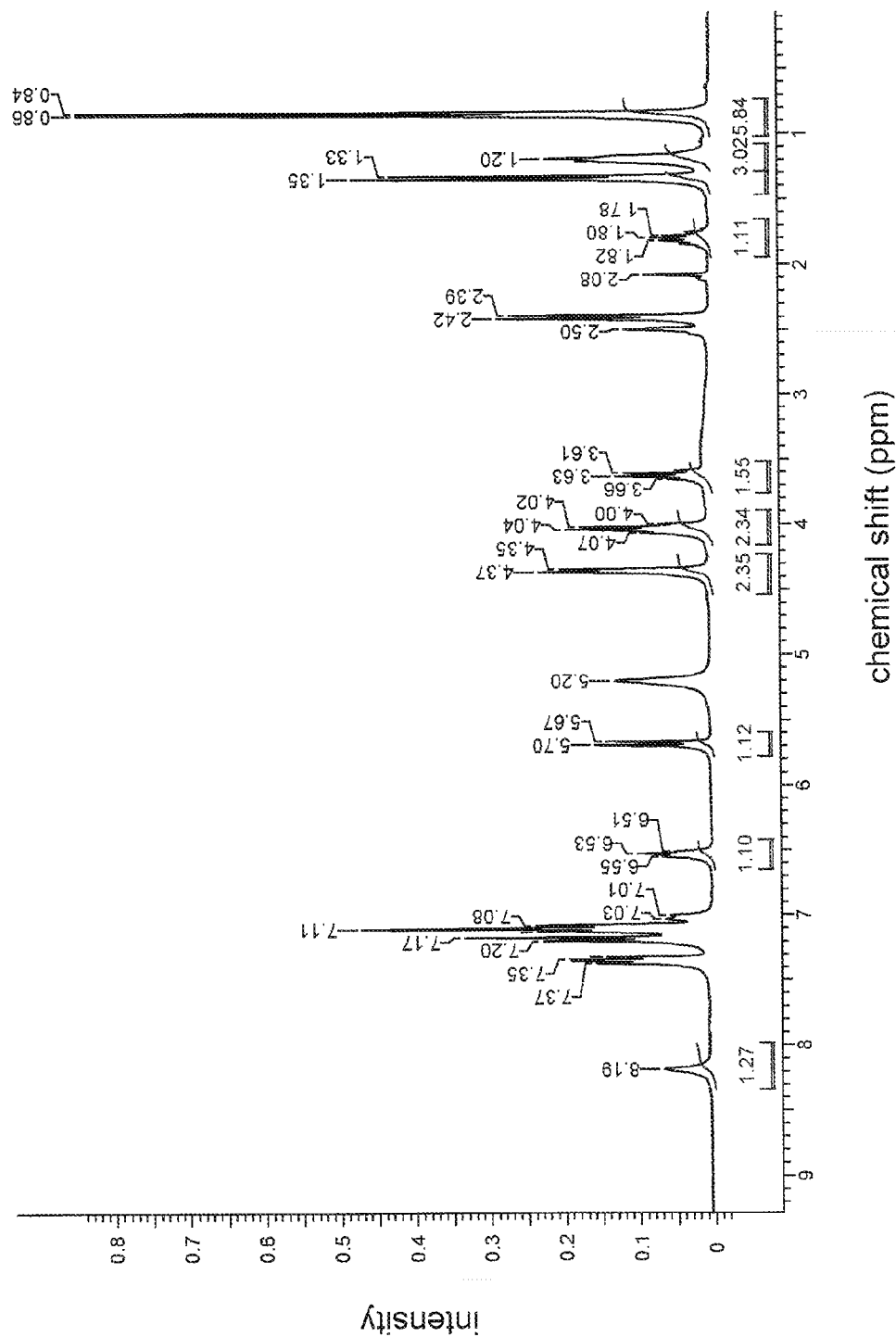
Figure 11:
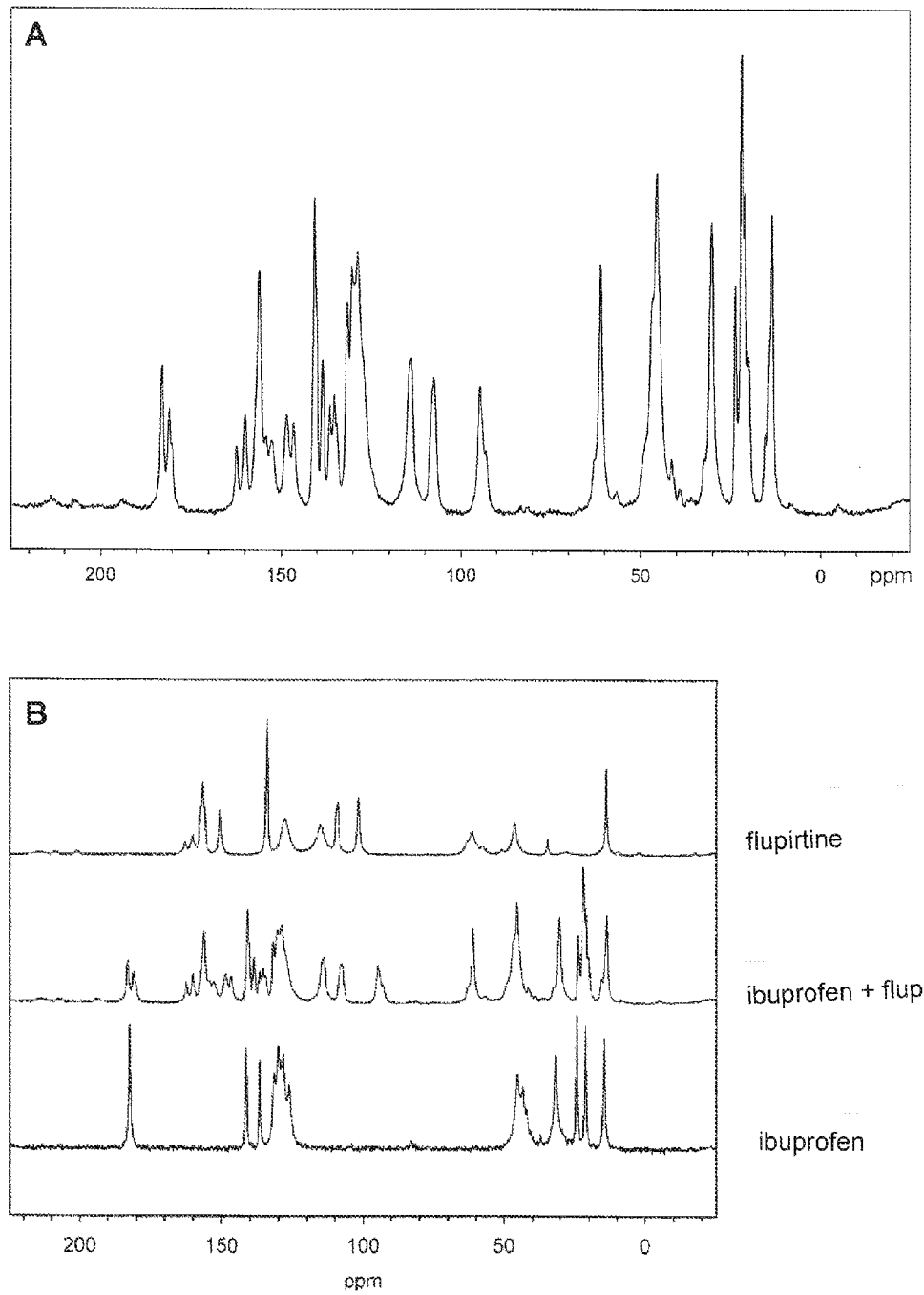
Figure 12:
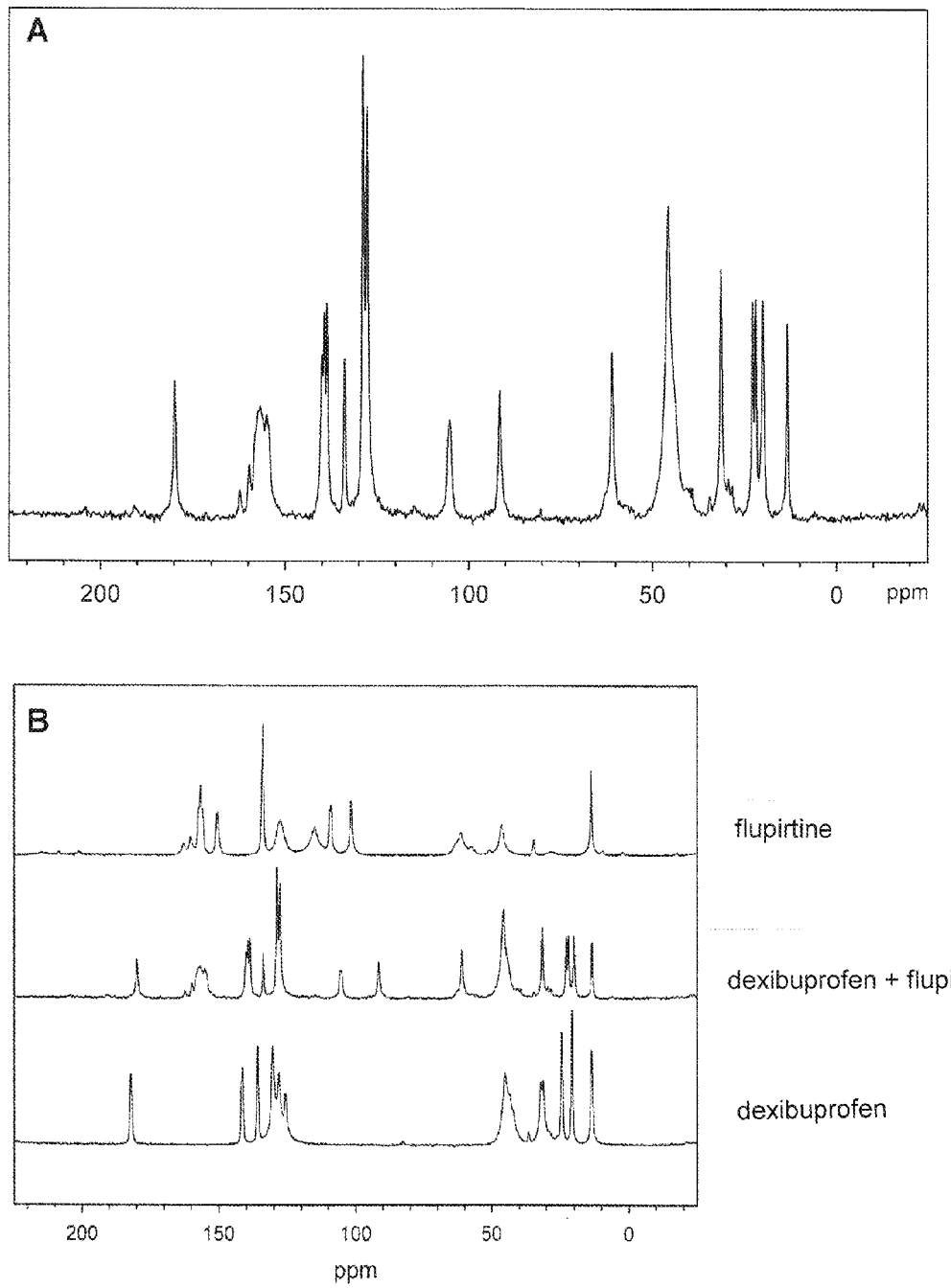
Figure 13:
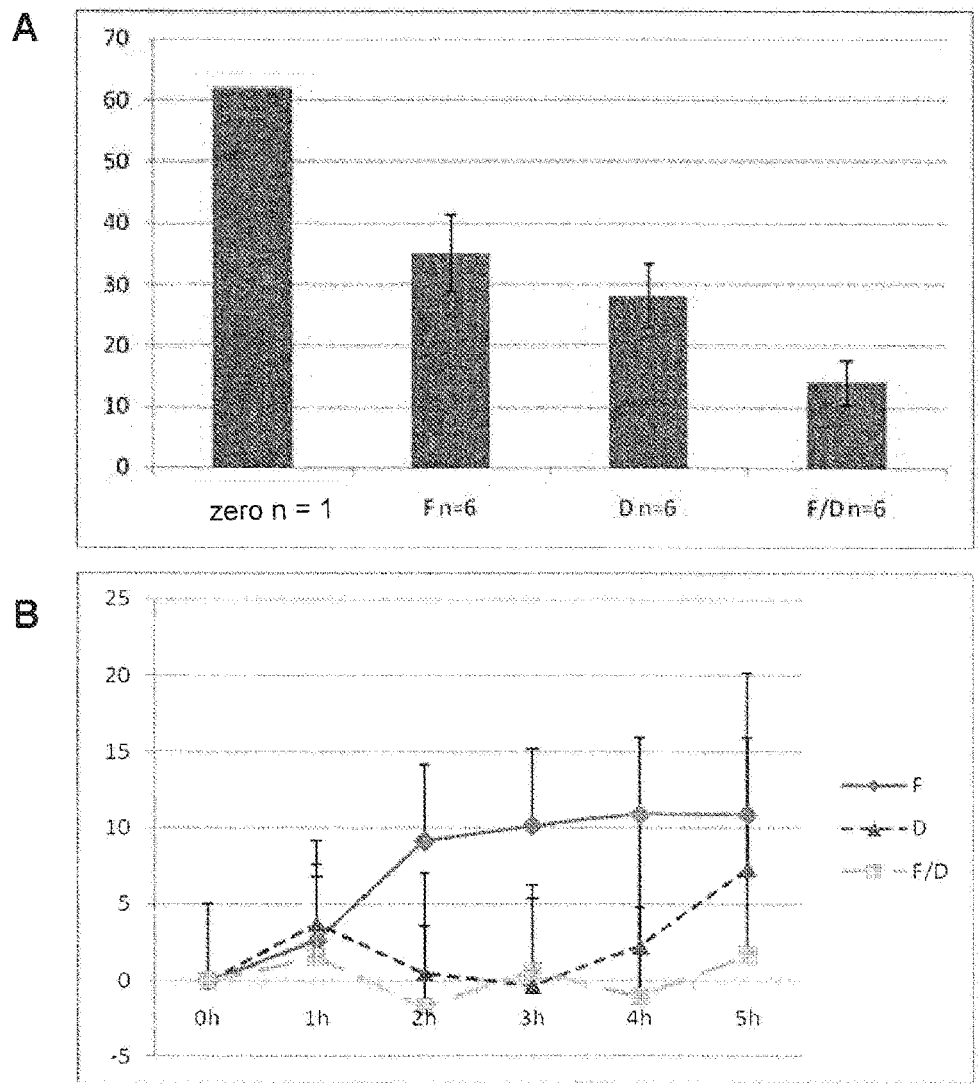

With the aid of the following figures and embodiments the invention will be explained in more detail without limiting it. It is shown in:

FIG. 1 an X-ray powder diffractogram of multicomponent crystals of flupirtine and ibuprofen in the range of 3°-40° 2θ;

FIG. 2 a comparison of the X-ray powder diffractogram of the multicomponent crystal of flupirtine and ibuprofen and its starting components flupirtine or ibuprofen;

FIG. 3 an X-ray powder diffractogram of the multicomponent crystal of flupirtine and dexibuprofen in the range of 1.5°-40°2θ;

FIG. 4 a comparison of the X-ray powder diffractograms of the multicomponent crystal of flupirtine and dexibuprofen and its starting components flupirtine and dexibuprofen;

FIG. 5 an DSC (differential scanning calorimetry) thermogram of the multicomponent crystal of flupirtine and ibuprofen in the temperature range of −40-300° C.;

FIG. 6 a DSC (differential scanning calorimetry) thermogram of the multicomponent crystal of flupirtine and dexibuprofen in the temperature range of 20-300° C.;

FIG. 7 an IR (infrared) spectrum of the multicomponent crystal of flupirtine and ibuprofen;

FIG. 8 an IR (infrared) spectrum of the multicomponent crystal of flupirtine and dexibuprofen;

FIG. 9 an $^1$H NMR spectrum (DMSO-d6, 400 MHz) of the multicomponent crystal of flupirtine and ibuprofen;

FIG. 10 an $^1$H NMR spectrum (DMSO-d6, 400 MHz) of the multicomponent crystal of flupirtine and dexibuprofen;

FIG. 11 a $^{13}$C CPMAS NMR spectrum of the multicomponent crystal of flupirtine and ibuprofen (A) and a comparison with the $^{13}$C CPMAS NMR spectrum of the starting materials (B);

FIG. 12 a $^{13}$C CPMAS NMR spectrum of the multicomponent crystal of flupirtine and dexibuprofen (A) and a comparison with the $^{13}$C CPMAS NMR spectrum of the starting materials (B); and FIG. 13 the analgesic effect of control (=zero), flupirtine (=F), dexibuprofen (=D) as well as of the multicomponent crystal of F and D (=F/D) on the writhing model of the mouse (10 mg per kg or 5 mg per kg each for HD) (FIG. 13A) and the antiphlogistic effect of flupirtine (=F), dexibuprofen (=D) as well as of the multicomponent crystal of F and D (=F/D) on the carrageenan model of the rat footpad (10 mg per kg each) or 5 g per kg each for F/D (FIG. 13B).

EMBODIMENTS

Example 1

Preparation of a Multicomponent Crystal of Flupirtine and Ibuprofen

A multicomponent crystal of flupirtine and ibuprofen according to the invention was prepared as follows:

In argon atmosphere, 12.0 h flupirtine ((([2-amino-6-(4-fluoro-benzylamino)-pyridin-3-yl]carbamic acid ethyl ester) and 8.24 g ibuprofen ((RS)-2-[4-(2-methylpropyl)-phenyl]propanoic acid) were added to 100 ml 2-propanol. The mixture was heated to 60° C. A clear solution was formed which was maintained for 30 minutes at 60° C. Subsequently, the solution was cooled to 20° C. and the solvent was slowly removed under vacuum (12 mmHg) at room temperature. The remaining product was dried for 12 h at 4 mm Hg in order to remove solvent residues. 19.8 g (98%) of a viscous yellow resin were obtained.

The glass transition temperature of the product is between −10 and 0° C. An IR spectrum (KBr) is shown in FIG. 7, an $^1$H NMR spectrum (DMSO-d6, 400 MHz) of the product is shown in FIG. 9, and a $^{13}$C CPMAS NMR is shown in FIG. 11

Example 2

Preparation of a Multicomponent Crystal of Flupirtine and Dexibuprofen

A multicomponent crystal of flupirtine and dexibuprofen according to the invention was prepared as follows:

In argon atmosphere, 12.0 g flupirtine ((([2-amino-6-(4-fluoro-benzylamino)-pyridin-3-yl]carbamic acid ethyl ester) and 8.24 g dexibuprofen ((+)-(2S)-2-[4-(2-methylpropyl)-phenyl]propanoic acid) were added to 100 ml acetone. The mixture was heated 50° C. whereby a clear solution was formed which was maintained for 30 minutes at 50° C. Subsequently, the solution was cooled to 20° C. and was dried for 24 h under vacuum (12 mm Hg). Thereby, 20.1 g (99.0%) of a viscous yellow resin were obtained.

The glass transition temperature of the product is between −10 and 0° C. An IR spectrum (KBr) of the product is shown in FIG. 8, an $^1$H NMR spectrum (DMSO-d6, 400 MHz) in FIG. 10, and a $^{13}$C CPMAS NMR in FIG. 12.

Example 3

Analysis of the Multicomponent Crystals by Means of X-Ray Powder Diffraction

The X-ray powder diffraction analysis of the compounds obtained according to Example 1 or 2 was carried out by means of a D8 Advance powder diffractometer of the company Bruker AXS whose specifications together with the measuring parameters are compiled in the following table.

TABLE 1

| Device specifications and measuring parameters for the X-ray powder diffraction ||
|---|---|
| Device specifications ||
| Monochromator | Johansson germanium single crystal |
| Detector | PSD LynxEye data recording report 4° 2θ |
| Sample carrier | Capillary sample carrier with a capillary diameter of 0.5 mm |
| Measuring parameters ||
| Radiation | Cu K$_{\alpha 1}$ |
| Generator | 40 kV, 40 mA |
| Angle range | 3° to 80° 2θ |
| Step width | 0.00922° 2θ |
| Measuring duration | 3 seconds/step |

The X-ray powder diffractograms that are generated in this way are shown in FIGS. 1 to 4. The signal positions of the X-ray powder diffractograms for the multicomponent crystal obtained according to Example 1 of flupirtine and ibuprofen are compiled in Table 2.

TABLE 2

Signal positions of the X-ray powder diffraction spectrum: for flupirtine-ibuprofen according to Example 1

| °2θ | Intensity/Cps | Relative intensity/% |
|---|---|---|
| 3.43 ± 0.2 | 69 | 100 |
| 8.29 ± 0.2 | 35 | 51 |
| 10.06 ± 0.2 | 29 | 42 |
| 12.46 ± 0.2 | 11 | 16 |

TABLE 2-continued

Signal positions of the X-ray powder diffraction spectrum:
for flupirtine-ibuprofen according to Example 1

| °2θ | Intensity/Cps | Relative intensity/% |
|---|---|---|
| 14.41 ± 0.2 | 8 | 12 |
| 16.73 ± 0.2 | 19 | 28 |
| 17.47 ± 0.2 | 37 | 55 |
| 20.71 ± 0.2 | 18 | 26 |
| 24.22 ± 0.2 | 16 | 23 |

The signal positions of the X-ray powder diffractogram for the muiticomponent crystal obtained according to Example 2 of flupirtine and dexibuprofen are compiled in Table 3.

TABLE 3

Signal positions of the X-ray powder diffraction spectrum for flupirtine-dexibuprofen of Example 2

| °2θ | Intensity/Cps | Relative intensity/% |
|---|---|---|
| 4.66 ± 0.2 | 235 | 100 |
| 5.08 ± 0.2 | 34 | 14 |
| 7.69 ± 0.2 | 17 | 7 |
| 9.30 ± 0.2 | 20 | 9 |
| 10.44 ± 0.2 | 21 | 9 |
| 18.00 ± 0.2 | 34 | 15 |
| 20.63 ± 0.2 | 33 | 14 |
| 27.28 ± 0.2 | 20 | 8 |

Example 4

Analysis of the Multicomponent Crystal by Means of DSC (Differential Scanning Calorimetry; Dynamic Differential Calorimetry)

The thermograms of the compounds obtained according to Examples 1 and 2 were measured by NETZSCH DSC 204 F1 Phönix. The specifications are provided in Table 4.

TABLE 4

Device specifications and measuring parameters for DSC (dynamic differential calorimetry)

Device specifications

| | |
|---|---|
| Measuring sensor | τ sensor |
| Furnace | Silver block with miniature jacket heating element |
| Cooling system | Mechanical cooling (intracooler) |
| Sample carrier | Aluminum sample crucible (pierced lid), crucible diameter 6 mm |

Measuring parameters

| | |
|---|---|
| Heating rate | 5° C./min. |
| Temperature program | 20° C.-300° C. |
| Inert gas | Nitrogen |
| Gas flow rate | 20 ml/min. |
| Sample mass | 11.242 mg |

The evaluation of the thermograms was done by the program Proteus (version 4.8.5) of the company NETZSCH. The obtained thermograms are shown in FIGS. 5 and 6.

Example 6

Analysis of the Ulticomponent Crystal by Means of $^{13}C$ CP/MAS NMR

All spectra were measured on an Avance 400 (company BRUKER, Rheinstetten) at a $^{13}C$ resonance frequency of 100.62 MHz. During measuring, the samples were rotated in a 4 mm double resonance sample head at a rotation frequency of 10.0 kHz ("magic angle spinning", MAS). For the CP experiment ("cross polarization"; CP), a $^1H$ 90° pulse of 5.3 μs and a contact pulse of 10 ms duration were used. The spectral width was 250 ppm (25,252 Hz).

13,000 FIDS with a repetition rate of 5.0 s were accumulated. In this connection, 1,600 data points were recorded and Fourier-transformed with a total point number of 16,384 ("zero-filling").

The chemical shift relates to tetramethyl silane (TMS, $s_{TMS}$=0.0 ppm). As a reference, after each experiment adamantane as a secondary external standard was measured ($S_{adamantane}$=28.72, 37.77 ppm). The signal positions of the $^{13}C$ CP/MAS NMR spectrum of the multi-component crystal obtained according to Example 1 of flupirtine and ibuprofen are compiled in Table 5.

TABLE 5

Signal positions of the $^{13}C$ CP/MAS NMR spectrum for flupirtine-ibuprofen of Example 1 [ppm]

| |
|---|
| 181.0 |
| 180.2 |
| 148.8 |
| 148.7 |
| 140.7 |
| 94.7 |
| 30.3 |
| 23..8 |
| 22.0 |

The signal positions of the $^{13}C$ CP/MAS NMR spectrum for the multicomponent crystal obtained according to Example 2 of flupirtine and dexibuprofen are compiled in Table 6.

TABLE 6

Signal positions of $^{13}C$ CP/MAS NMR spectrum for flupirtine-dexibuprofen of Example 2 [ppm]

| |
|---|
| 179.8 |
| 156.8 |
| 155.1 |
| 105.4 |
| 91.6 |
| 23.0 |
| 22.2 |
| 20.1 |

Example 7

Tablets Containing 300 mg of the Multicomponent Crystal According to the Invention of Flupirtine and an Arylpropionic Acid Selected from Ibuprofen and Dexibuprofen The multicomponent crystals obtained according to Example 1 or 2 were comminuted by air jet milling (jet mill). For this purpose, the active ingredient was cooled prior to the milling process to 150 Kelvin by means of liquid nitrogen. The entire milling process was done under nitrogen atmosphere. Prior to granulation the particle size distribution of the active ingredient was determined. In the desired size range (at least 90% by weight smaller than 200 flm), the determination by air jet sieving (for example Alpine air jet sieve) is particularly well suited. Should the desired particle size distribution not be obtained with one sieving step, the milling step was repeated accordingly. The milled active ingredient was loved through a 0.5 mm sieve (destruction of agglomerates) and then filled into a cube mixer. To 100 parts of sieved active ingredient 1 to 10 parts of hydroxypropyl cellulose (HPC) and 1 to 10 parts of amorphous silicon dioxide were added. The powders were mixed with each other for 5 minutes. Subsequently, 4 parts of sieved magnesium stearate were added and the entire powder mixture was then mixed again for 15 minutes. The powder mixture was subsequently pressed by means of a rotary tablet press to oblong tablets.

Example 8

Soft Capsules Containing 300 mg of a Multicomponent Crystal of Flupirtine and Dexibuprofen According to the Invention 300 mg of the multicomponent crystal of flupirtine and dexibuprofen produced according to Example 2 were mixed, optionally with light heating, with 300 mg of diethylene glycol monoethyl ether, 100 mg of polyethylene glycol, and 15 mg of polyvinyl pyrrolidone and 10 mg Labrasol® and filled into soft gelatine capsules (size 8 minims).

Example 9

Analgesic Effect and Anti-Inflammatory Effect of a Multicomponent Crystal of Flupirtine and Dexibuprofen According to the Invention a) Analgesic Effect Based on the Writhing Test the Mouse
The analgesic effect was determined by standard animal test model of the mouse. In the so-called "writhing test" an 0.8% acetic acid solution is applied intraperitoneally 30 minutes after application of the test substances. The number of writhing reactions of the body is then counted; their reduction serves as an expression of analgesic action.

The test substances (control=zero, flupirtine=F, dexibuprofen=D, multicomponent crystal of F and D=F/D) were administered orally in a dosage of 10 mg per kg body weight.

In FIG. 13 A an unequivocal and significant decrease of the number of writhing reactions of the body can be recognized which is most pronounced after administration of the multicomponent crystal according to the invention.
b) Antiphlogistic Test Based on Carrageenan Test on the Rat
The inflammation-triggering substance carrageenan is applied to the footpad of the rat's foot as a 1% solution (0.1 ml) 60 minutes after oral administration of the test substances. The development of the resulting footpad edema is measured over a time period of 5 hours after administration of carrageenan. As an expression of an antiphlogistic effect, a reduced development of the edema is expected. The multicomponent crystal according to the invention (multicomponent crystal of F and D=F/D) as well as the individual components (flupirtine=F, dexibuprofen=D, control=zero) were administered in a single dose of 10 mg per kg wherein the single dose of the multicomponent crystal according to the invention was 5 mg per kg.

As can be seen in FIG. 13 B, for the administration of a single dose of the multicomponent crystal according to the invention a reduced development of footpad edema of the rat is observed compared to the administration of dexibuprofen or flupirtine.

What is claimed is:
1. Multicomponent crystal, characterized in that it contains as a sole active ingredient combination a combination of:
([2-amino-6-(4-fluoro-benzylamino)-pyridin-3-yl]carbamic acid ethyl ester (flupirtine) and
the arylpropionic acid
(RS)-2-[4-(2-methylpropyl)-phenyl]propanoic acid (ibuprofen),
and further characterized by an X-ray powder diffractogram with a characteristic peak at $2\theta=4.7\pm0.2°$.

2. Multicomponent crystal according to claim 1, additionally characterized by characteristic peaks at $2\theta=5.1\pm0.2°$, $7.7\pm0.2°$, $9.3\pm0.2°$ and $10.4\pm0.2°$.

3. Multicomponent crystal according to claim 1, additionally characterized by characteristic peaks at $2\theta=18.0\pm0.2°$, $20.6\pm0.2°$, and $27.3\pm0.2°$.

4. Multicomponent crystal according to claim 1, wherein the arylpropionic acid (RS)-2-[4-(2-methylpropyl)-phenyl] propanoic acid is characterized by a DSC (differential scanning calorimetry) thermogram with a melting endothermal peak in the range of 56 to 70° C. with an onset temperature at $56.9\pm2$ C.° and a signal maximum at $64.7\pm3°$ C.

5. Multicomponent crystal, characterized in that it contains as a sole active ingredient combination a combination of:
([2-amino-6-(4-fluoro-benzylamino)-pyridin-3-yl]carbamic acid ethyl ester (flupirtine) and
the arylpropionic acid (+)-(2S)-2-[4-(2-methylpropyl)-phenyl]propanoic acid (dexibuprofen),
and further characterized by an X-ray powder diffractogram with a characteristic peak at $2\theta=3.4\pm0.2°$.

6. Multicomponent crystal according to claim 5, additionally characterized by characteristic peaks at $2\theta=8.3\pm0.2°$, $10.1\pm0.2°$, $16.7\pm0.2°$, $17.5\pm0.2°$, and $20.7\pm0.2°$.

7. Multicomponent crystal according to claim 5, additionally characterized by characteristic peaks at $2\theta=12.5\pm0.2°$, $14.4\pm0.2°$, and $24.2\pm0.2°$.

8. Multicomponent crystal according to claim 5, wherein the arylpropionic acid (+)-(2S)-2-[4-(2-methylpropyl)-phenyl]propanoic acid is characterized by a DSC (differential scanning calorimetry) thermogram with a melt endothermal peak in the range of 73 to 85° C. with an onset temperature at $75.9\pm2°$ C. and a signal maximum at $81.4\pm3°$ C.

9. Method for preparing a multicomponent crystal according to claim 1, comprising the steps:
a) dissolving flupirtine and the arylpropionic acid (RS)-2-[4-(2-methylpropyl)-phenyl]propanoic acid (ibuprofen) in a molar ratio of 1.0:0.9 to 1.0 to 1.1 in an inert organic solvent, and
b) crystallizing the multicomponent crystal.

10. Pharmaceutical preparation containing a multicomponent crystal according to claim 1 as active ingredient.

11. Oral pharmaceutical preparation according to claim 10 in the form of a soft capsule.

12. Pharmaceutical preparation according to claim 10, wherein the pharmaceutical preparation contains 50 to 1,000 mg per administration unit of a multicomponent crystal according to claim 1 as active ingredient.

13. Transdermal pharmaceutical preparation containing a multicomponent crystal according to claim 1 as active ingredient.

14. Method for preparing a pharmaceutical preparation, comprising mixing of a multicomponent crystal according to claim 1 with a solvent on the basis of glycol, a solutizer, and a viscosity-imparting agent such as PVP and introducing the mixture into a soft gelatine capsule.

15. Method for preparing a multicomponent crystal according to claim 5, comprising the steps:
   a) dissolving flupirtine and the arylpropionic acid (+)-(2S)-2-[4-(2-methylpropyl)-phenyl]propanoic acid (dexibuprofen) in a molar ratio of 1.0:0.9 to 1.0 to 1.1 in an inert organic solvent, and
   b) crystallizing the multicomponent crystal.

16. Pharmaceutical preparation containing a multicomponent crystal according to claim 5 as active ingredient.

17. Oral pharmaceutical preparation according to claim 16 in the form of a soft capsule.

18. Pharmaceutical preparation according to claim 16, wherein the pharmaceutical preparation contains 50 to 1,000 mg per administration unit of a multicomponent crystal according to claim 1 as active ingredient.

19. Transdermal pharmaceutical preparation containing a multicomponent crystal according to claim 5 as active ingredient.

20. Method for preparing a pharmaceutical preparation, comprising mixing of a multicomponent crystal according to claim 5 with a solvent on the basis of glycol, a solutizer, and a viscosity-imparting agent such as PVP and introducing the mixture into a soft gelatine capsule.

\* \* \* \* \*